United States Patent [19]

Bundy et al.

[11] Patent Number: 5,001,234
[45] Date of Patent: Mar. 19, 1991

[54] CYCLIC HYDROCARBONS WITH AN AMINOALKYL SIDECHAIN

[75] Inventors: Gordon L. Bundy; Gilbert A. Youngdale, both of Portage, Mich.

[73] Assignee: The Upjohn Company, Kalamazoo, Mich.

[21] Appl. No.: 435,481

[22] PCT Filed: Apr. 1, 1988

[86] PCT No.: PCT/US88/00978

§ 371 Date: Oct. 16, 1989

§ 102(e) Date: Oct. 16, 1989

[87] PCT Pub. No.: WO88/08002

PCT Pub. Date: Oct. 20, 1988

Related U.S. Application Data

[63] Continuation-in-part of Ser. No. 62,276, Jun. 15, 1987, abandoned, which is a continuation-in-part of Ser. No. 39,042, Apr. 16, 1987, abandoned.

[51] Int. Cl.$^5$ .............................................. C07J 41/00
[52] U.S. Cl. ..................................... 540/106; 552/521
[58] Field of Search ................... 540/106; 260/397.3, 260/397.4; 514/106; 552/521

[56] References Cited

U.S. PATENT DOCUMENTS

| | | | |
|---|---|---|---|
| 3,284,475 | 11/1966 | Klimstra | 260/397.4 |
| 3,370,070 | 2/1968 | Klimstra | 260/397.3 |
| 4,239,780 | 12/1980 | Wallach | 424/330 |

FOREIGN PATENT DOCUMENTS 8702367  4/1987  World Int. Prop. O.

OTHER PUBLICATIONS

W. Vogt, Advances in Prostaglandins and Thromboxane Research, 3:89–95 (1978).
R. J. Flower et al., Nature, 278:456–459 (1979).
L. Kaplan et al., Proc. Natl. Acad. Sci., 75:2955–2988 (1978).
E. Vallee et al., J. Pharm. Pharmacol., 31:588–592 (1974).
M. Roberts et al., J. of Biol. Chem., 252:2405–2411 (1977).
Blackwell et al., British J. Pharmacy, 62:79–89 (1978).
D. P. Wallach and V. J. R. Brown, Bioch. Pharmacol., 30:1315–1324 (1981).
L. J. Griggs, "Part I. Synthetic Approaches to 5- and 16-Thiaestrone. Part II. Estrone with a Diazacholesterol Side Chain," University of Michigan (1965).
P. D. Klimstra et al., J. Med. Chem., 9:323–326 (1966).

Primary Examiner—Cecilia Shen
Assistant Examiner—Celia Chang
Attorney, Agent, or Firm—Debbie K. Wright; Paul J. Koivuniemi

[57] ABSTRACT

This invention provides novel cyclic hydrocarbons of the formula:

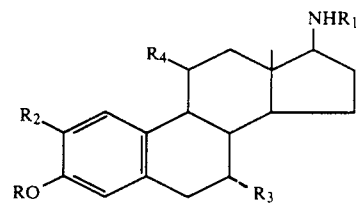

wherein R is selected from the group consisting of $CH_2=CH-CH_2-$, $HO-CH_2CH_2CH_2-$, and $CH_3$;
wherein $R_1$ is selected from the group consisting of m-trifluoromethylphenylmethyl, 2-thienylmethyl, and p-aminosulfonylphenylethyl;
wherein $R_2$ and $R_3$ are methyl or hydrogen;
wherein $R_4$ is hydrogen or —OH;

a compound of the formula

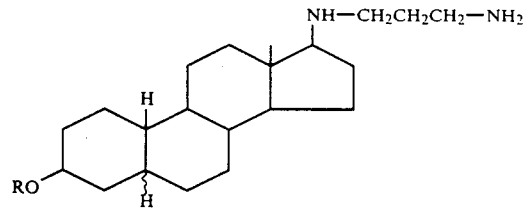

wherein R is $(CH_3)_2NCH_2CH_2CH_2-$ or $NH_2CH_2CH_2CH_2-$;

or a compound of the formula

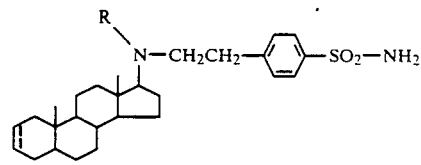

wherein the dashed line indicates that the 2-3 bond is saturated or unsaturated and, wherein R is hydrogen or methyl.

These compounds are useful for inhibiting adverse physiological symptoms associated with phospholipase $A_2$ and for treating hyperglycemia associated diseases such as diabetes and obesity.

6 Claims, No Drawings

CYCLIC HYDROCARBONS WITH AN AMINOALKYL SIDECHAIN

CROSS REFERENCE TO RELATED APPLICATION

This application is a continuation-in-part of application Ser. No. 062,276, filed Jun. 15, 1987, now abandoned, which is a continuation-in-part of application Ser. No. 039,042, filed Apr. 16, 1987, now abandoned.

FIELD OF INVENTION

This invention encompasses novel cyclic hydrocarbons substituted with an aminoalkyl sidechain that are useful for inhibiting adverse physiological symptoms associated with phospholipase A2 and for treating hypoglycemia associated diseases such as diabetes and obesity.

BACKGROUND

Phospholipase A2 hydrolyses arachidonic acid containing phospholipids, thereby providing substrate to the multiple enzymes of the arachidonic acid cascade. The metabolites of the arachidonic acid cascade are varied and include prostaglandins, thromboxanes, leukotrienes, or other hydroxylated derivatives of arachidonic acid. The role of phospholipase A2 in the formation of prostaglandins in mammalian metabolism is well known, see W. Vogt, Advances in Prostaglandins and Thromboxane Research, 3, p. 89 (1978) and P. C. Isakson, et al., Advances in Prostaglandin and Thromboxane Research, 3, page 113, (1978). Generally, these metabolites are beneficial but in certain disease processes or other conditions the excessive production of arachidonic acid metabolites causes deleterious consequences such as inflammation, erythema, platelet aggregation, or allergic responses. The inhibition of phospholipase A2 prevents these and similar conditions.

The actual inhibition of phospholipase A2 takes place on a cellular level, therefore, administration of phospholipase A2 inhibitory compounds can be by any manner that will allow for phospholipase A2 inhibition in the affected tissues or organs. The precise mechanisms of the disease processes or conditions which stimulate the arachidonic acid cascade are not clearly understood. The essential prerequisite, however, is enhanced activity of the phospholipases which provide arachidonate to the series of reactions designated as the arachidonic acid cascade. One aspect of the present invention is to block the action of the phospholipases and cut off the flow of arachidonic acid into the cascade, irrespective of the stimulus or stimuli which may be present. Thus, the inhibition of phospholipase A2 of this invention is suitable for treating seemingly unrelated diseases whose common element is the stimulation of the arachidonic acid cascade.

Hyperglycemia refers to a condition commonly found in patients suffering from mature onset diabetes mellitus or other diseases which cause impairment of pancreatic function. Hyperglycemic patients with non-insulin dependent diabetes mellitus (NIDDM) with insulin resistance exhibit elevated serum glucose levels. Failure to adequately control elevated serum glucose levels can cause myocardioischemia, stroke, peripheral vascular disease, lethargy, coma, blindness, kidney failure or death. One important means of treating these patients uses oral antidiabetic agents instead of conventional treatment for hyperglycemic conditions such as restriction of carbohydrate intake or insulin injection.

INFORMATION DISCLOSURE

Some inhibitors of phospholipase A2 are known. Certain local anesthetics have been shown to inhibit phospholipase A2 activity by competing with calcium ion, which appears to be necessary for phospholipase activity. see W. Vogt, Advances in Prostaglandin and Thromboxane Research, 3, p. 89 (1978) and E. Vallee et al., J. Pharm. Pharmacol., 31, pp. 588-592 (1974). R. J. Flower and G. J. Blackwell have shown that certain anti-inflammatory steroids induce biosynthesis of a phospholipase A2 inhibitor which prevents prostaglandin generation, see Nature, 278, p. 456 (1979). These steroids are not direct inhibitors of phospholipass A2, but rather stimulate the synthesis of a phospholipase inhibiting factor called lipocortin, lipomodulin, or macrocortin.

Some direct phospholipase A2 inhibitors are known. Indomethacin, a drug with anti-inflammatory properties, has been shown to inhibit phospholipase A2 enzymes isolated from the venoms of Russell's Viper, *Crotalus adamanteus*, and bee, and from pig pancreas; see K. L. Kaplan, et al., Proc. Natl. Acad. Sci., 75, pp. 2955-2988 (1978). Bromphenacyl bromide has been shown to inhibit phospholipase A2 by acylating a histidine residue which is at the active site of the enzyme; see M. Roberts, et al., J. of Biol. Chem., 252, pp. 2405-2411 (1977). Mepacrine has been shown to inhibit the activity of phospholipase A2 derived from perfused guinea pig lung, see R. Blackwell, et al., British J. Pharmacy, 62, p. 79-89 (1978). Some butyrophenones are disclosed as phospholipase A2 inhibitors in U.S Pat. No. 4,239,780. D. P. Wallach and V. J. R. Brown. Bioch. Pharmacol. 30, pp. 1315-1324 (1981) also refer to several compounds that inhibit phospholipase A2.

U.S. Pat. No. 3,370,070 discloses amino-substituted steroid compounds which are useful as hypocholesterolemic agents, antibacterial, anti-protozoal, and anti-algal agents. The doctoral thesis of L. J. Griggs, "Part I. Synthetic Approaches to 5- and 16-Thiaestrone. Part II. Estrone with a Diazacholesterol Side Chain," University of Michigan (1965) discloses amino-substituted steroid compounds with potential hypocholesterolemic activity. U.S. Pat. No. 3,284,475 and P. D. Klimstra, et al., "Hypocholesterolemic Agents-VI. A- And B-Ring-Modified Azacholesterols", J. Med. Chem., 9, pp. 323-326 (1966) also disclose amino-substituted steroid compounds.

SUMMARY OF THE INVENTION

The present invention is: compounds of formula I wherein R is selected from the group consisting of $CH_2=CH-CH_2-$, $HO-CH_2CH_2CH_2-$, and $CH_3$, wherein $R_1$ is selected from the group consisting of formulas IV-VI, wherein $R_2$ and $R_3$ are methyl or hydrogen, wherein $R_4$ is hydrogen or hydroxy and pharmacologically acceptable salts thereof; compounds of formula II wherein R is $(CH_3)_2NCH_2CH_2CH_2-$ or $NH_2CH_2CH_2CH_2-$ and pharmacologically acceptable salts thereof; and compounds of formula III wherein the dashed line indicates that the 2-3 bond is saturated or unsaturated and wherein R is hydrogen or methyl.

Compounds represented by formula II are useful when it is medically necessary or desirable to inhibit phospholipase A2 in a mammalian system. They are particularly useful in treating symptoms or conditions resulting from metabolites produced by the arachidonic acid cascade, hereafter PMC (phospholipase mediated conditions). PMC includes all untoward conditions or symptoms which are the result of the excessive stimulation of the arachidonic acid cascade. These conditions include allergic diseases, inflammatory conditions (including chronic inflammatory conditions such as rheumatoid arthritis), burns, and hypoxic conditions at the cellular level such as coronary infarcts or infarcts of other tissues. In infarct conditions it is desirable to block phospholipase A2 activity to prevent the destruction of the phospholipids which are integral structural components of cellular membranes.

Compounds represented by formulas I and III invention are useful as hypoglycemic agents in treating patients suffering from elevated serum glucose levels resulting from an impairment of tissue response to insulin and/or an impairment of pancreatic islet function such as non-insulin dependent diabetes mellitus (NIDDM) with insulin resistance.

DETAILED DESCRIPTION

The dosage regimen for preventing or treating phospholipase mediated conditions, PMC, by the compounds represented by formula II are selected in accordance with a variety of factors, including the type, age, weight, sex, medical condition of the mammal, severity of the PMC and the particular compound employed. An ordinarily skilled physician or veterinarian will readily determine and prescribe the effective amount of the compound to prevent or arrest the progress of the condition. Typically, the physician or veterinarian employs relatively low dosages at first and then increases the dose until a desired or maximum response is obtained. Because the diseases or conditions caused by the arachidonic acid cascade are varied, methods of administering these compounds to patients must depend on the particular PMC to be treated. Preferred patients to be treated are domesticated animals and humans, the most preferred patients are humans.

Regardless of the route of administration selected, the compounds used are formulated into pharmaceutically acceptable dosage forms by conventional methods known to the pharmaceutical art. Thus, the compounds can be administered orally in forms such as pills, capsules, solutions or suspensions; rectally or vaginally in forms such as suppositories or bougies; parenterally, either subcutaneously, intravenously, or intramuscularly using sterile injectable forms known to the pharmaceutical art. For treatment of conditions such as erythema the compounds of this invention may also be administered topically in the form of ointments, creams, gels, or the like.

Initial dosages of the compounds of this invention are from about 0.003 to 3.0 g per 70 kg mammal per 6-8 hours orally. When other forms of administration are employed, equivalent doses are administered. When dosages beyond 45 mg/kg are employed, care should be taken with each subsequent dose to monitor possible toxic effects.

The phospholipase A2 inhibitory compounds of the present invention ameliorates the cellular damage resulting from the degradation of cell membranes by phospholipase A2 after hypoxic states such as coronary infarcts, ligation of the aorta during surgery for aortic aneurysms (resulting in kidney damage), and the like, see Zalewski. et al., Clinical Research 31, p. 227 (1983). Preferred patients to be treated are domesticated animals and humans, the most preferred patients are humans. This is a preferred use of these compounds.

The phospholipase A2 inhibitory compounds are useful in the treatment of asthma. Asthma is a lung disease in which a wide variety of stimuli can result in an asthmatic attack. These stimuli could be damp cold air or allergens in the environment. The asthmatic response is initially characterized by constriction of the bronchioles leading to increased airway resistance. This early constrictive phase is due to mast cell release of histamine and other modulators such as peptides. After the constrictive phase, a late sustained phase occurs which, in human beings, may reach a maximum in 6-8 hours. This phase is slower in onset and disappearance and is due to metabolites of the arachidonic acid cascade such as thromboxanes, prostaglandins, and leukotrienes, see "Corticosteroid Treatment in Allergic Airway Diseases", Proceedings of a Symposium in Copenhagen Oct. 1-2, 1981 (Editors: T. H. Clark, N. Myginfd, and O. Selroos, Munksgaard/Copenhagen 1982). Inhibition of phospholipase A2 at a physiologically acceptable level will prevent formation of these products in the lung thought to be responsible for the "2nd wave" of airway resistance. Preferred patients to be treated are domesticated animals and humans, the most preferred patients are humans.

For these uses, the compounds are administered in a variety of dosage forms: orally in the form of tablets, capsules, or liquids; rectally in the form of suppositories; parenterally, subcutaneously, intradermally, or intramuscularly, with intravenous administration being preferred in emergency situations, by inhalation in the form of aerosols or solutions for nebulizers; or by insufflation in the form of powder. These compounds are effectively administered to human asthma patients by oral or aerosol inhalation.

Doses in the range of about 0.01 to 50 mg per kg of body weight are used 1 to 4 times a day, the exact dose depending on the age, weight, condition of the patient and frequency and route of administration. For the above use these compounds can be combined advantageously with other anti-asthmatic agents, such as sympathomimetics (isoproterenol, phenylephrine, ephedrine); xanthine derivatives (theophylline, aminophylline); and corticosteroids (prednisolone).

Administration by oral inhalation with conventional nebulizers or by oxygen aarosolization conveniently provides the active ingredient in dilute solution. preferably at concentrations of about 1 part of medicament to from about 100 to 200 parts of weight of total solution. Entirely conventional additives may be employed to stabilize these solutions or to provide isotonic media, for example, sodium chloride, sodium citrate, citric acid, sodium bisulfite, and the like can be employed.

A self propelled dosage unit suitable for inhalation therapy for administering the active ingredient in aerosol form comprises the active ingredient suspended in an inert propellant such as a mixture of dichlorodifluoromethane and dichlorotetrafluoroethane together with a co-solvent such as ethanol, flavoring materials and stabilizers. Instead of a co-solvent, a dispensing agent such as oleyl alcohol can also be used. Suitable means to employ the aerosol inhalation therapy technique are described fully in U.S. Pat. No. 2,868,691.

The compounds represented by formula II also control spasm and facilitate breathing in conditions such as bronchial asthma, bronchitis, bronchiectasis, pneumonia and emphysema. To treat a patient with these symptoms, the compounds would be administered to the patient in the same manner as described above. This is a preferred use of compounds represented by formula II.

These novel phospholipase A2 inhibitory compounds are also useful as anti-inflammatory agents in mammals, especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 g per kg per min until relief from pain is attained. When these novel compounds are administered orally, they are formulated as tablets, capsules, or as liquid preparations, with the usual pharmaceutical carriers, binders, and the like. For intravenous use, sterile isotonic solutions are preferred.

These novel phospholipase A2 inhibitory compounds are useful whenever it is desired to inhibit platelet aggregation, reduce the adhesive character of platelets, or remove or prevent the formation of thrombi in mammals. For example, these compounds are useful to prevent myocardial infarcts, to prevent post-operative thrombosis to promote patency of vascular grafts following surgery, or to treat conditions such as atherosclerosis, arteriosclerosis, blood clotting defects due to lipemia, and other clinical conditions. Preferred patients to be treated are domesticated animals and humans, the most preferred patients are humans. For these uses, these compounds are administered intravenously, subcutaneously, intramuscularly, or in the form of sterile implants for prolonged action. For rapid response especially in emergency situations, the intravenous route of administration is preferred. Doses in the range about 0.005 to about 20 mg per kg of body weight per day are used, the exact dose depending on the age, weight, condition of the patient, and frequency and route of administration.

Phospholipase A2 Inhibitors of the present invention are useful in the treatment or prevention of conditions due to increased phospholipase activity observed after central nervous system (CNS) trauma such as brain and spinal cord injury, see, E.P. Wei, et al., J. Neurosurg., 56, pp. 695-698 (1982) and E. D. Hall and J. M. Braughler, Surgical Neurology, 18, pp. 320-327 (1982). Preferred patients to be treated are domesticated animals and humans, the most preferred patients are humans.

The compounds represented by formula II are useful to treat PMC symptoms which have already occurred in the mammal or to prevent PMC symptoms in particularly susceptible mammals. Use of these compounds before the development of PMC symptoms prevents the formation of the prostaglandins and similar products causing such conditions. Thus, phospholipase inhibitors of the present invention are used to prevent edema and erythema from sunburn by administering these compounds prior to exposure to sunlight. These compounds are also administered to persons suffering from hayfever or similar allergies prior to exposure to the allergenic substances to which hayfever sufferers are sensitive.

It is most preferred to use the compounds of this invention in the treatment or prevention of asthma and in the treatment or prevention of cellular death resulting from hypoxic states. The preferred route in most cases is to systemically administer the compounds in order to allow them to enter the mammal's bloodstream and thus be distributed throughout the mammal's system. In certain cases, where the PMC is of a localized nature (sunburn or psoriasis), topical administration is employed in order that the phospholipase A2 inhibition is confined to the afflicted area.

While conventional treatment for hyperglycemic conditions may include restriction of carbohydrate intake and insulin injection, one important means of treating hyperglycemic patients is with oral hypoglycemic agents.

Compounds of this invention represented by formulas I and III are useful to treat NIDDM and its complications in mammals, including human beings because these compounds lower the serum glucose levels when administered to $KKA^y$ mice with spontaneous diabetes. Accordingly, a patient to be treated with certain of the novel hypoglycemic compounds of this invention is first diagnosed as a diabetic by conventional means, usually by the persistence of elevated serum glucose levels, and a treatment regimen with compounds of this invention is established so that the elevation in a patient's serum glucose level is either significantly reduced or eliminated. The precise therapeutic endpoint of treatment, elimination or merely reduction in hyperglycemia, is readily determined by the attending physician based upon the clinical presentation and concomitantly employed treatment. For example, certain of the novel hypoglycemic compounds of this invention may be employed to significantly reduce hyperglycemia in a patient, with a carbohydrate-restricted diet providing a further measure of control. Preferred patients to be treated are domesticated animals and humans, the most preferred patients are humans.

While the novel hypoglycemic compounds of this aspect of the invention may be administered by any convenient route; orally, subcutaneously, intravenously, intramuscularly, topically, or rectally, these compounds are most significantly and usefully employed as oral hypoglycemic agents, particularly in solid dosage form such as capsules and tablets. Alternatively, liquid oral dosage forms, such as syrups and elixirs, are alternatively employed. The solid, oral pharmaceutical compositions in accordance with the present invention are all prepared by methods known in the art for preparing other oral antidiabetic compositions. Since an individual patient response to treatment with compounds in accordance with the present invention may vary, effective dosages of the compounds of the instant invention will vary from patient to patient. Ordinarily, an oral dosage of from 0.1 to 10 mg/kg of these compounds will be adequate to significantly reduce hyperglycemia in a patient being treated. Repeated dosages, every 4-12 hr, may be required during the day to maintain the antihyperglycemic effect. Accordingly, dosages from about 0.1 mg/kg/dose to about 10 mg/kg/dose, depending upon the patient, frequency of treatment, and observed response. An attending physician may at first prescribe a relatively small amount of a novel hypoglycemic compound of this invention and later increase this dosage as necessary to achieve the desired level of control.

Novel hypoglycemic compounds of the present invention are also useful to treat and/or prevent obesity in mammals including human beings. For this purpose, the novel compounds of this invention are formulated and administered as described above for hyperglycemia.

All compounds of the present invention may be formulated into pharmaceutical compositions, employing a pharmaceutically acceptable carrier. Pharmaceutical formulations include pharmaceutical compositions suitable for oral, parenteral, vaginal, topical, and rectal use, such as tablets, powder packets, cachets, dragees, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Coconut oil, sesame oil, safflower oil, cottonseed oil, peanut oil may be used for preparing solutions or suspensions. Sweetening, coloring and flavoring agents may be added.

In general the preferred route of administration depends on the condition being treated. For asthma, oral or aerosol inhalation is preferred. For most other conditions the preferred mode of administration is oral.

The phospholipase A2 inhibitory compounds of this invention are useful in any mammal whose metabolic system includes the phospholipase. induced arachidonic acid cascade. The mammals which are preferred. are generally domesticated animals and humans. Humans are the most preferred mammals to be treated.

The utility of the compounds of this invention represented by formula II is demonstrated in the following laboratory tests which determine phospholipase inhibition.

Inhibition of Rat Neutrophil Aggregation

1. Method for Thioglycolate Broth Preparation

Weigh sufficient thioglycolate medium, USP grade, to prepare a 5% w/v solution in sterile water. Heat the solution for 10 minutes on a boiling water bath. Remove and allow the solution to cool to 20°-25°. Inject 10±0.5 ml intraperitoneally into Sprague-Dawley rats as described below.

2. Method for Rat Peritoneal Leukocyte Collection

Six (6) Sprague-Dawley, pathogen free, female rats (230-270 grams) are injected intraperitoneally with 10.0±0.5 ml thioglyco. late broth. 5% w/v 16.18 hours prior to sacrifice. After sacrifice by cervical dislocation, leukocytes accumulated in the peritoneal cavity are collected by injecting 30 ml of sterile 0.9% w/v sodium chloride intraperitoneally and vigorously massaging the abdomen to assure uniform dispersion of the cells within the carcass. Use a pasteur pipet to remove approximately 20 ml of fluid with suspended cells from a small incision through the abodominal wall. Collect the cell suspension in plastic culture tubes.

3. Washing and Resuspension of Cells for Aggregation

Centrifuge the cell suspensions isolated above for 10 minutes at 1000 rpm (Sorvall RC.3, HG-4L rotor, 25° C.). Discard the supernatant. Resuspend the cells evenly in 0.9% NaCl to original volume, centrifuge a second time for 10 minutes at 1000 rpm. Discard the supernatant. Resuspend the cells evenly in Hanks buffer.

4. Determination of Leukocyte Concentration

Transfer 10 μl of leukocyte suspension into a plastic cell counting cup. Add 15.0 ml of ISOTON~ diluent for cell counting. Determine the cell count with a Model ZBI Coulter Counter or equivalent.

5. Neutrophil Aggregation

A. Add 0.5 ml of rat leukocyte (neutrophil) suspension to each channel of a Payton dual channel aggregometer. Cuvettes 45 mm×4 mm i.d., are used. Cell suspensions at 37° C. are stirred (400 rpm).

B. Add 5 μl test compound (0.01M in absolute ethanol) to cell and evaporate to dryness under nitrogen. Add 0.5 ml cell suspension (37° C. 400 rpm). Incubate for 2 minutes, then add 1 μl of the agonist. $10^{-4}$M FMLP.

C. Record the aggregation trace (% transmitted light) on a potentiometric recorder.

Inhibition of Hog Pancreas PLA$_2$

1. Enzymes

Both soybean lipoxidase and hog pancreas phospholipase A$_2$ are obtained commercially from Sigma. The soybean lipoxidase is dis. solved at a concentration of 5 mg/ml in 0.033 M ammediol-HCl buffer pH 8.5 with $1 \times 10^{-4}$M Ca$^{++}$. The hog pancreas enzyme is added at the rate of approximately 350 units per ml of final mixture. Thus, 0.025 ml is equivalent to 9 units of phospholipase and 0.125 mg of lipoxidase.

2. Substrate

The substrate is phosphatidyl choline. The material has a fatty acid composition upon saponification, of 2% of 16:0, 1% of 18:0, 3% of 18:1, 18% of 18:2, and 12% of 18:3 fatty acids with the largest fraction being linoleic acid. The estimated molecular weight is 780.

78 mg of this substrate is put in a 10 ml volumetric flask containing 100 mg of deoxycholic acid. A "pill" magnetic stirrer is added along with 7-8 ml of water, and the whole stirred rapidly until all the lecithin is dissolved. The "pill" is then removed and the flask contents are made up to 10 ml with water.

3. Procedure

To three oxygraph cells equipped with magnetic stirrers is added 2.5 ml of 0.033M ammediol-HCl buffer, pH 8.5, containing $1 \times 10^{-4}$M Ca$^{++}$. This is followed by 0.1 ml of the inhibitors made up at an initial concentration of 0.01M in methanol. Where controls are run, 0.1 ml of methanol is added to each cell. The cells are then put in the oxygraph apparatus and the contents are stirred briefly. 0.025 ml of the enzyme mixture is then added and the electrodes are inserted in each cell, care being taken to exclude all air bubbles. With the stirrer and water bath pump on, the contents of each cell are stirred for 2.5 minutes at 37.5° C. The reaction is initiated by adding to the cells 0.05 ml of 0.01M lecithin substrate. The reaction is monitored by continuous measurement of rates of oxygen depletion from the medium as a consequence of unsaturated fatty acids (linoleic acid) being released from esterified form by the phospholipase. These fatty acids immediately become substrates for the soybean lipoxidase which forms the 15-hydroxy acids, with consequent oxygen utilization.

The initial rates of oxygen consumption are recorded using a Sargeant-Welch Recorder set at 5 mV full scale. The "air" setting and medium chart speed are used. The slopes of oxygen consumption are then determined in triplicate, and these are compared with the methanol controls to determine the degree of inhibition. If complete inhibition is seen at the first concentration, appropriate dilutions are made to bring the inhibition percentages down to at least 3 concentrations of inhibitor where partial inhibition is observed. The $I_{50}$ can then be calculated for that particular inhibitor, using linear regression slopes. All compounds for which $I_{50}$ value is shown are tested for inhibitory activity on the soybean lipoxidase. None inhibit at the test concentration.

The utility of the compounds of this invention represented by formulas I and III is demonstrated in the following laboratory tests which determine serum glucose levels in mice.

Testing For Blood Glucose Lowering In The KKA$^y$ Mouse

1. General

All KKA$^y$ mice used for screening are produced and selected by methods previously outlined, T. Fujita et al., Diabetes, 32 804–10 (1983). Groups of 6 animals each are employed.

2. Screening Procedure

Pre-treatment nonfasting blood glucose (NFBG) samples are measured 5 days prior to the start of a screening run by previously described methodologies. These blood sugar values are used to place animals into groups with equal mean blood glucose concentrations and to eliminate any mice with a NFBG value <250 mg/dl. On day 0, compounds chosen to be run are incorporated into ground mouse chow (Purina 5015). Compounds are included at a rate of 1 mg/gram of chow. Generally, 300 g of drugs containing diet is prepared for each group. Mice receiving ground chow only are the negative control. Each screening run also uses ciglitazone (T. Fujita, et al., supra) as a positive control (0.5 to 1.0 mg/gram chow).

Initial body and food weights are taken on day 1. Food is placed in a crock which contains an adequate amount to last for the length of the study. In order to acclimate the mice from pelleted mouse chow to ground mouse chow, they are fed the ground chow for 9 days prior to use in the screen. On day 4 of treatment, a NFBG sample is again measured, as well as food and body weights. Food consumption measurements are used to determine an average mg/kg dose the mice received over the testing period, and to evaluate the compound's effect on food consumption.

3. Acceptance of a Screening Run and Determination of Activity

Acceptance and activity are determined by the following criteria:

A. Negative Control

This group must not show a significant change ($p < 0.05$) from pre- to post-treatment. If there is a significant decrease in blood sugar the run is not valid.

B. Positive Control

This group must show a significant depression in blood sugar mean levels from pre- to post-treatment. A lack of activity in this group would also invalidate the run.

C. Negative Control vs. Positive Control

This contrast must be significant. It is a further assurance that both control groups performed as expected.

D. Compound

A compound's activity is based on several criteria:
(1) A significant decrease in blood sugar mean levels from pre- to post-treatment.
(2) Negative control vs. compound: This contrast allows one to determine if these groups are dissimilar, which is required for the compound to be considered active.

General syntheses of compounds similar to those of the present invention are set forth in PCT application PCT/US86/02116, filed 7 October 1986, which is incorporated herein by reference.

A bond indicated as "~" includes both the $\alpha$ and $\beta$ configurations.

Compounds that have been found to have a phospholipase A$_2$ inhibitory or antidiabetic effect as determined by at least one of the above assays are indicated in the Examples and Preparations which follow by the notation "PLA2" and/or "diabetes" respectively.

EXAMPLES

Preparation 1

17$\beta$-t-Butyldimethylsilyloxy-19-nor-androstan-3-one

A 250 ml, 3-necked flask, equipped with a magnetic stirrer, was flame dried and then cooled in a nitrogen atmosphere. The flask was charged with 10 g of 17$\beta$-hydroxy-5$\alpha$-estran-3-one dissolved in 150 ml of dimethylformamide. The solution was treated with 3.7 g of imidazole and the solution was cooled to 0° C. The solution was then treated with 6.5 g of t-butyldimethylsilylchloride and allowed to stir at room temperature for 48 hours. The reaction mixture was diluted with water and extracted twice with hexane/ethyl acetate (9:1). The combined organic layers were washed with brine, dried over anhydrous magnesium sulfate and concentrated in vacuo.

The crude product (14.6 g) was flash chromatographed on 90 g of 230–400 mesh silica gel. The column was packed and eluted with (91:9) hexane/ethyl acetate with (no column volume eluted) 30 ml fractions collected. Based on their TLC homogeneity, fractions 4–13 were combined affording 14 g of the title compound. m.p. 103°–104° C.

Preparation 2

17$\beta$-t-Butyldimethylsilyl-19-nor-androstan-3,17-diol

A 2000 ml, 3-necked flask, equipped with a magnetic stirrer, was flame dried and then cooled in a nitrogen atmosphere. The flask was charged with 14 g of the title compound from Preparation 1 dissolved in 850 ml of methanol/methylene chloride (15:2). The solution was treated with 7 g of sodium borohydride in small portions. The reaction mixture was allowed to stir for 15 minutes. The reaction mixture was quenched with 2M NaHSO$_4$, diluted with water and extracted with ethyl acetate. The organic layer was washed with water, washed with brine, dried over anhydrous magnesium sulfate, and concentrated in vacuo.

The crude product (15.3 g) was chromatographed on 1000 g of 230. 400 mesh silica gel. The column was packed and eluted with (98:2) methylene chloride/acetone. An initial fraction of 1200 ml was collected followed by 17 ml fractions. Based on their TLC homogeneity, fractions 280–430 were combined affording 10.9 g (77% of theory) of the title compound ($\beta$isomer). m.p. 135°–138° C.

Preparation 3

3-[[(3$\beta$,5$\alpha$)-17-[(t-Butyldimethylsilyl)oxy]estran-3-yl]oxy]propanenitrile A 250 ml, 3-necked flask, equipped with a magnetic stirrer, was flame dried and then cooled in a nitrogen atmosphere. The flask was charged with 8.0 g of 3β alcohol steroid from Preparation 2 dissolved in 150 ml of benzene. The solution was treated with 2.2 ml of freshly distilled acrylonitrile followed by 0.37 ml of Triton B and the reaction mixture was stirred at room temperature for 72 hours. The reaction mixture was washed with dilute HCl, washed with water, dried over anhydrous magnesium sulfate and concentrated in vacuo.

The crude product (10.9 g) was chromatographed on 1070 g of 230–400 mesh silica gel. The column was packed and eluted with (83:17) hexane/ethyl acetate. An initial fraction of 1500 ml was collected followed by 18 ml fractions. Based on their TLC homogeneity, fractions 81–110 were combined affording 7.0 g of the title compound, NMR (CDCl$_3$, TMS): δ3.8–3.4 (m), 3.4–3.0 (br). 2.7–2.45 (t), 2.2–0.4 (m), 0.9 (s) and 0.75 ppm (s).

Preparation 4

3-[[(3β,5α)-17-[hydroxy]estran-3-yl]oxyl]propanenitrile

A 500 ml, 3-necked flask, equipped with a magnetic stirrer, was flame dried and then cooled in a nitrogen atmosphere. The flask was charged with 4.4 g (9.9 mmol) of 3β-cyano ether from Preparation 3 dissolved in 500 ml of methylene chloride and 200 ml of methanol. The solution was treated with 32 ml (102 mmol) of a 3.2M HCl in methanol solution. The reaction mixture was allowed to stir at room temperature for 30 min. The reaction mixture was diluted with water and extracted with ethyl acetate. The organic layer was washed again with water, washed with brine, dried over anhydrous magnesium sulfate and concentrated in vacuo.

The crude product (3.73 g) was flash chromatographed on 90 g of 230–400 mesh silica gel. The column was packed and eluted with (98:2) methylene chloride/acetone (no column volume eluted) with 25 ml fractions collected. Based on their TLC homogeneity, fractions 8–25 were combined affording 3.1 g of the title compound. NMR (CDCl$_3$, TMS): δ 3.75–3.4 (m), 3.4–3.0 (br, 2.6–2.3 (t), 2.15–0.75 (m) and 0.75 ppm (s).

Preparation 5

3[[(3β,5α)-17-estran-one]oxy]propanenitrile

A 50 ml, 3-necked flask, equipped with a magnetic stirrer, was flame dried and then cooled in a nitrogen atmosphere. The flask was charged with 1.0 g of 3β-17-hydroxy steroid from Preparation 4 dissolved in 20 ml of acetone and the solution was cooled to 0° C. The solution was treated with 1.0 ml of Jones reagent reaction and the mixture was stirred for 15 minutes. The reaction mixture was quenched with 5 ml of 2-propanol. The reaction mixture was diluted with water and extracted with ethyl acetate. The organic layer was washed with water, washed with brine, dried over anhydrous magnesium sulfate, and concentrated in vacuo, to give 1.1 g of the title compound. NMR (CDCl$_3$, TMS): δ 3.8–3.55 (t, 2H), 3.5–3.1 (br, 1H), 2.8–2.45 (t, 2H), 2.45–0 95 (m) and 0.9 ppm (s, 3H).

Preparation 6

N-[(3β,5α)-3-((3-propanenitrile)oxy)estran-17-yl]-1,3-propanediamine

A 50 ml, 2-necked flask, equipped with a magnetic stirrer, was flame dried and then cooled in a nitrogen atmosphere. The flask was charged with 0.36 ml of 1,3-diaminopropane dissolved in 10 ml of methanol. The pH of the solution was adjusted to 6.0 with glacdial acetic acid. The solution was then treated with 282 mg of 3β-steroid from Preparation 5 and followed by 75 mg of sodium cyanoborohydride. The reaction mixture was refluxed for 18 hours. The reaction mixture was basified with concentrated ammonium hydroxide and then concentrated in vacuo.

The crude product (3.29 g) was chromatographed on 100 g of 230–400 mesh silica gel. The column was packed and eluted with (92.3:7.0:0.7) chloroform/methanol/ammonia. An initial fraction of 150 ml was collected, followed by 6 ml fractions. Based on their TLC homogeneity, fractions 45–180 were combined affording 250 mg of the title compound. NMR (CDCl$_3$, TMS) δ 3.75–3.55 (t, 2H), 3.4–3.0 (br, 1H), 2.8–0.75 (m) and 0.65 ppm (s, 3H).

Preparation 7

N-(3β, 5α)3-(3-aminopropoxy)estran-17-ol

A 250 ml, 3-necked flask, equipped with a magnetic stirrer, was flame dried and then cooled in a nitrogen atmosphere. The flask was charged with 105 mg of lithium aluminum hydride slurried in 30 ml of diethyl ether. The solution was treated with 230 mg of 3β-ether-17-hydroxy steroid from Preparation 4 dissolved in 50 ml of diethyl ether and the reaction mixture was refluxed for 2 hours. The reaction mixture was quenched with 0.21 ml of water followed by 0.17 ml of a 10% sodium hydroxide solution and the reaction mixture was allowed to stir at room temperature for 18 hours. The reaction mixture was filtered and the solids washed several times with hot chloroform. The filtrate was concentrated in vacuo.

The crude product (350 mg) was flash chromatographed on 90 g of 230–400 mesh silica gel. The column was packed and eluted with (92.3:7.0:0.7) chloroform/methanol/ammonia. An initial 5–15 ml fractions were collected followed by 30 ml fractions. Based on their TLC homogeneity, fractions 8–14 were combined affording 175 mg of the title compound NMR (CDCl$_3$, TMS): δ 3.56–3.51 (t, 2H), 3.25–3.1 (br, 1H), 2.8–2.77 (t, 2H), 2.05–0.92 (m and 0.74 ppm (s, 3H).

Preparation 8

N-(3β,5α)-3-(3-aminopropoxy)estran-17-one

A 25 ml, 2-necked flask, equipped with a magnetic stirrer, was flame dried and then cooled in a nitrogen atmosphere. The flask was charged with 170 ml of 3β-aminoether-17-hydroxy steroid from Preparation 7 dissolved in 5 ml of acetone and then cooled to 0° C. The solution was treated with 27 μl (0.51 mmol) of concentrated sulfuric acid followed by 0.31 ml of Jones reagent and was allowed to stir for 1 hour. The reaction mixture was quenched with 2 ml of 2-propanol followed by 0.6 g of sodium citrate dihydrate and a small piece of amalgamated zinc (Org. Syn. Coll., Vol. IV, p. 696 (1963). The reaction mixture was allowed to stir for 30 minutes at room temperature. The reaction mixture was basified with 3 MKOH (pH 10) and the aqueous layer saturated with sodium chloride. The aqueous layer was extracted 5 times with methylene chloride, 2 times with chloroform and once with diethyl ether. The aqueous layer was then stirred vigorously with methylene chloride. The combined organic extracts were dried over anhydrous magnesium sulfate and concentrated in vacuo.

The crude product (85 mg) was chromatographed on 8 g of 230–400 mesh silica gel. The column was packed and eluted with (92.3:7.0.:0.7) chloroform/methanol- /ammonia. An initial fraction of 5 ml was collected followed by 0.8 ml fractions. Based on their TLC homogeneity, fractions 23-40 were combined affording 45 mg of the title compound. Infrared: $\lambda_{max}$ (chloroform solution) 2950, 2850 and 1740 cm$^{-1}$ (PLA2)

Preparation 9

N-[(3β,5α)-3-[3-(dimethylamino)propoxy]estran-17-one]

A 10 ml, 2-necked flask, equipped with a magnetic stirrer, was flame dried and then cooled in a nitrogen atmosphere. The flask was charged with 44 mg of 3β-aminoether-17-keto-steroid from Preparation 8 dissolved in 1 ml of dioxane. The solution was treated with 1.3 ml of a 1.0 M monosodium phosphorous acid solution followed by 98 μl of 37% formaldehyde. The reaction mixture was then heated at 60° C. for 2 hours. The reaction mixture was diluted with methylene chloride and water. The aqueous layer was basified with 3M KOH to a pH of 11. The organic layer was separated and the aqueous layer was re-extracted 2 times with methylene chloride. The combined organic layers were washed with brine, dried over anhydrous magnesium sulfate and concentrated in vacuo.

The crude product (36 mg) was not chromatographed. Based on TLC, crude product was determined to be relatively pure title compound. NMR (CDCl$_3$, TMS): δ 3.6-3.4 (m), 3.3-2.8 (m), 2.7 (s), 2.6-0.4 (m) and 0.8 ppm (s).

EXAMPLE 1

3-Methoxy-17β-[(2-thienylmethyl)amino]-estra-1,3,5-(10)-triene

A solution of 7.96 g of 2-thiophsnemethylamine in 50 ml of MeOH and 150 ml of THF was acidified with 6 ml (6.29 g) of glacial acetic acid. Then 10 g of estrone methyl ether was added. The mixture was heated until a solution was obtained and then stirred at ambient temperature for 1 hour. Sodium cyanoborohydride (2.18 g) was added. The resulting solution was stirred for 5 hours. An additional 2.18 g of sodium cyanoborohydride was added. The stirring was continued for 17 hours. The solvent was evaporated. The residue was treated with 200 ml of H$_2$O and basified with a 50% NaOH solution. The mixture was extracted with CH$_2$Cl$_2$ (3×100 ml). The combined extracts were washed with 50 ml of brine and dried over MgSO$_4$. Evaporation of the solvent left 17.54 g of oil. The oil was chromatographed on a 1100 g column of silica gel. The column was eluted with 7.5% MeOH-CH$_2$Cl$_2$ and 200 ml fractions were collected. The fractions were assayed by silica gel TLC (1×4") (5% MeOH-CH$_2$Cl$_2$). Fractions 14-22 were combined and crystallized from CH$_2$Cl$_2$-hexane affording 9.0 g of the title compound as clusters of pale yellow needles. m.p. 85.5-5.87°. (diabetes)

EXAMPLE 2

3-Allyloxy-17β-[((3-trifluoromethyl)phenylmethyl)-amino-estra-1,3,5(10)-triene Fumarate A solution of 4 g of 3-(trifluoromethyl)benzylamine in 25 ml of MeOH and 75 ml of THF was acidified with 3 ml (3.15 g) of acetic acid. Then 5 g of 3-allyloxyestrone was added. After a solution was obtained, 1.2 g of sodium cyanoborohydride was added. The resulting solution was stirred for 3 hours. An additional 1.2 g of NaCNBH$_3$ was added. The stirring was continued for 66 bours. The solvent was evaporated. The residue was treated with 200 al of H$_2$O basified with 50% NaOH solution, and extracted with CH$_2$Cl$_2$ (3×100 ml). The combined extracts were washed with 50 ml of brine and dried over MgSO$_4$. Evaporation of the solvent left a pale yellow oil. The oil was chromatographed on a 700 g column of silica gel. The column was eluted with 10% acetone CH$_2$Cl$_2$ and 200 ml fractions were collected. The fractions were assayed by silica gel TLC (1×4")(10% acetone. CH$_2$Cl$_2$). Fractions 9-18 were combined giving 6.83 g of a pale yellow oil. A solution of the 6.83 g of oil in 100 ml of acetone was added to a solution of 1.68 g (14.47 mmoles) of fumaric acid in 30 ml of EtOH. The solution was concentrated and then hexane was added. Cooling gave 7.56 of the title compound as s white solid, m.p. 171°-174°. (diabetes)

EXAMPLE 3

3-(3-Hydroxypropoxy)-17β-[((3-trifluoromethyl)-phenylmethyl)amino-estra-1,3,5(10)-triene Fumarate (1:1)

A solution of 2.5 g of 3-(trifluoromethyl)benzylamine in 25 ml of MeOH and 75 ml of THF was acidified with 3 ml (3.15 g) of acetic acid. Then 2.37 g of 3-(3-hydroxypropoxy)-estra-1,3,5(10) trien-17-one was added. After a solution was obtained, 1.2 g of sodium cyanoborohydride was added. The resulting solution was stirred for 4 hours. An additional 1.2 g of NaCNBH$_3$ was added. The stirring was continued for 18.5 hours. The solvent was evaporated. The residue was treated with 200 ml of H$_2$O basified with 50% NaOH solution, and extracted in the CH$_2$Cl$_2$ (3×100 ml). The combined extracts were washed with 50 ml of brine and dried over MgSO$_4$. Evaporation of the solvent left a pale yellow oil. The oil was chromatographed on a 400 g column of silica gel. The column was eluted with 25% acetone-CH$_2$Cl$_2$ and 100 ml fractions were collected. The fractions were assayed by silica gel TLC (1×4")(25% acetone-CH$_2$Cl$_2$). Fractions 16-23 were combined giving 2.94 g of a pale yellow oil. A solution of the 2.94 g (6.03 mmoles) of oil in 75 ml of acetone was added to a solution of 0.7 g (6.03 mmoles) of fumaric acid in 20 ml of EtOH. The solution obtained was concentrated and the hexane was added. Cooling gave 2.54 g (70%) of the title compound as a white solid, m.p. 117°-121°. (diabetes)

EXAMPLE 4

3-Methoxy-7α-methyl-17β-[((3-trifluoromethyl)phenyl-methyl)amino-estra-1,3,5(10)-triene Fumarate Hydrate A solution of 3.32 g of 3-(trifluoromethyl)benzylamine in 25 ml of MeOH and 75 ml of THF was acidified with 3 ml (3.15 g) of acetic acid. Then 2.83 g of 7α-methylestrone methyl ether was added. After a solution was obtained, 1.2 g of sodium cyanoborohydride was added. The resulting solution was stirred for 6 hours. An additional 1.2 g of NaCNBH$_3$ was added. The stirring was continued for 17 hours. The solvent was evaporated. The residue was treated with 200 ml of H$_2$O, basified with 50% NaOH solution, and extracted with CH$_2$Cl$_2$ (3×100 ml). The combined extracts were washed with 50 ml of brine and dried over MgSO$_4$. Evaporation of the solvent left a pink oil. The oil was chromatographed on a 400 g column of silica gel. The column was eluted with 10% acetone-CH$_2$Cl$_2$ and 100 ml fractions were collected. The fractions were assayed by silica gel TLC (1×4")(10% acetone-CH$_2$Cl$_2$). Fractions 10-19 were combined giving 3.93 g of pale yellow oil. A solution of the 3.93 g of oil in 75 ml of acetone was added to a solution of 0.5 g (4.31 mmoles) of fumaric acid in 15 ml of EtOH. The mixture was reduced in volume to 40 ml. Then 100 ml of hexane was added. Cooling gave 2.79 g of the title compound as a white solid. m.p. 189°-190°. (diabetes)

Example 5

3-Methoxy-11β-hydroxy-17β-[((3-trifluoromethyl)-phenylmethyl) amino-estra-1,3,5(10)-triene A solution of 2.47 g of 3-(trifluoromethyl)benzylamine in 25 ml of MeOH and 75 ml of THF was acidified with 3 ml (3.15 g) of acetic acid. Then 2.12 g (7.06 mmoles) of 11β-hydroxyestrone methyl ether was added. After a solution was obtained, 1.2 g of sodium cyanoborohydride was added. The resulting solution was stirred for 6 hours. An additional 1.2 g of NaCNBH$_3$ was added. The stirring was continued for 18 hours. The solvent was evaporated. The residue was treated with 200 ml of H$_2$O, basified with 50% NaOH solution, and extracted with CH$_2$Cl$_2$ (3 × 100 ml). The combined extracts were washed with 50 ml of brine and dried over MgSO$_4$. Evaporation of the solvent left an oil. The oil was chromatographed on a 400 g column of silica gel. The column was eluted with 10% MeOH-CH$_2$Cl$_2$ and 100 ml fractions were collected. The fractions were assayed by silica gel TLC (1×4")(10% MeOH-CH$_2$Cl$_2$). Fraction 11 was crystallized from CH$_2$Cl$_2$-hexane giving 0.39 g of white needles. The 0.39 g was combined with fraction 12 and crystallized from CH$_2$Cl$_2$-hexane giving 1.06 g of the title compound as white needles. m.p. 122°-123°. (diabetes)

EXAMPLE 6

N-Methyl-17β-[2-(4-aminosulfonylphenyl)ethyl)amino]-5α-androstane

To a stirred solution of 3.45 g (7.52 mmoles) of crude 17β-[2-(4-aminosulfonylphenyl)ethyl]amino]-5α-androstane in 175 ml of THF and 125 ml of acetonitrile was added 3 ml (40 mmoles) of 37% formaldehyde solution and 1 g (15.91 mmoles) of sodium cyanoborohydride followed by 1 ml (1.05 g, 17.47 mmoles) of acetic acid. The mixture was stirred for 24 hours. The solvent was evaporated. The residue was treated with 200 ml of H$_2$O, basified with 50% NaOH solution, and extracted with CH$_2$Cl$_2$ (3 × 100 ml). The combined extracts were washed with 50 ml of brine and dried over MgSO$_4$. Evaporation of the solvent left 0.66 g of oil. The combined aqueous phases, which were milky, were acidified with acetic acid. The mixture was extracted with CH$_2$Cl$_2$ (3 × 100 ml). The combined extracts were washed with 50 ml of brine and dried over MgSO$_4$. Evaporation of the solvent left 3.3 g of solid. The 3.3 g appeared to be the acetate salt. A mixture of the 3.3 g, 100 ml of CH$_2$Cl$_2$, and 150 ml of 10% NaHCO$_3$ solution was stirred for 17 hours. The layers were separated. The CH$_2$Cl$_2$ layer was dried over MgSO$_4$. Evaporation of the solvent left 2.5 g of foamy solid. The aqueous layer was extracted with 100 ml of CH$_2$Cl$_2$. The extract was dried over MgSO$_4$. Evaporation of the solvent left 0.05 g of oil which was discarded. The 0.66 g and the 2.58 g were combined, dissolved in 50 ml of 1:1 acetone.CH$_2$Cl$_2$, and applied to a 400 g column of silica gel (packed in 1:1 acetone. CH$_2$Cl$_2$). The column was eluted with 1:1 acetone-CH$_2$Cl$_2$ and 100 ml fractions were collected. Fraction 13 was crystallized from CH$_2$Cl$_2$ Skelly B giving 0.39 g of solid. The 0.39 g was recrystallized from acetone Skelly B giving 0.16 g of solid. The 0.16 g was combined with fractions 14-22 and crystallized from CH$_2$Cl$_2$-hexane (cooled at room temperature overnight) giving a white solid. The solid was dried in a vacuum oven at 55° for 21 hours giving 1.46 g of the title compound, m.p. 168°-172° (diabetes)

EXAMPLE 7

2-Methyl-3-methoxy-17β-[2-(4-aminosulfonylphenyl)ethyl)amino]-estra-1,3,5(10)-triene A mixture of 2.54 g (8.51 mmoles) of 2-methyl-3-methoxyestra-1,3,5(10)-trien-17-one, 3.41 g (17.03 mmoles) of 4.(2.aminoethyl)benzenesulfonamide (Interchem. Corp), and 180 ml of MeOH was heated until a solution was obtained. Then 0.6 g (9.55 mmoles) of sodium cyanoborohydride was added. The resulting solution was stirred for 3 hours. Then 1 ml (1.05 g, 17.47 mmoles) of acetic acid was added. The mixture was stirred and refluxed for 44 hours. The solvent was evaporated. The residue was treated with a solution of 5 g of NaHCO$_3$ in 200 ml of H$_2$O and extracted with CH$_2$Cl$_2$ (3 × 100 ml). The combined extracts were washed with 50 ml of brine and dried over MgSO$_4$. Evaporation of the solvent left 4.03 g of solid. The solid was dissolved in 50 ml of 10% MeOH-CH$_2$Cl$_2$ and applied to a 400 g column of silica gel (packed in 10% MeOH-CH$_2$Cl$_2$). The column was eluted with 10% MeOH-CH$_2$Cl$_2$ and 100 ml fractions were collected. The fractions contained some solid, m.p. ca 230, which was insoluble in CH$_2$Cl$_2$ and H$_2$O but was soluble in MeOH. The solid was saved. Fractions 15-23 were combined in CH$_2$Cl$_2$ and filtered to remove insoluble material. The filtrate was concentrated and hexane was added. Cooling gave 2.80 g of white solid. The 2.80 g was recrystallized from acetone-hexane giving a white solid. The solid was dried in a vacuum oven at 54° for 17 hours giving 2.60 g of the title compound, m.p. 170-173. (diabetes)

EXAMPLE 8

17β-[2-(4-Aminosulfonylphenyl)ethyl)amino]-5α-androst-2-ene

A mixture of 4.32 g (15.86 mmoles) of 5α-androst-2-en-17-one, 4.76 g (23.17 mmoles) of 4.(2.aminoethyl)-benzenesulfonamide (Interch em Corp.), and 180 ml of MeOH was heated until a solution was obtained. Then 1 g (15.91 mmoles) of sodium cyanoborohydride was added followed by 1.5 ml (1.57 g, 26.2 mmoles) of acetic acid. The resulting solution was stirred and refluxed for 42 hours. The solvent was evaporated. The residue was treated with a solution of 5 g of NaHCO$_3$ in 200 ml of H$_2$O and extracted with CH$_2$Cl$_2$ (3 × 100 ml). The combined extracts were washed with 50 ml of brine and dried over MgSO$_4$. Evaporation of the solvent left 6.67 of solid. The solid was dissolved in 50 ml of 10% MeOH-CH$_2$Cl$_2$ and applied to a 400 g column of silica gel (packed in 10% MeOH-CH$_2$Cl$_2$). The column was eluted with 10% MeOH-CH$_2$Cl$_2$ and 100 ml fractions were collected. Fractions 15-25 were combined and dissolved in MeOH. Triethylamine (5 ml) was added followed by H$_2$O. The mixture was cooled in an ice bath. The somewhat gelatinous solid which separated was collected by filtration, washed with H$_2$O, and dried in a vacuum oven at 55° for 16 hours giving 6.1 g. The 6.1 g was crystallized from acetone-hexane giving a white solid. The solid was crushed and then dried in a vacuum oven at 54° for 65 hours giving 4.97 of the title compound, m.p. 158°-159.5°. (diabetes)

EXAMPLE 9

N-[(3β,5α)-3-(3-aminopropoxy)estran-17-yl]-1,3-propanediamine

A 500 ml Parr flask was charged with 195 mg of 3β-ether-17-aminopropyl steroid N-[(3β,5α)-3-((3-propanenitrile)oxy)estran-17-yl]-1,3-propanediamine dissolved in 25 ml of a 2.5M NH₃ in ethanol solution. The solution was treated with 100 mg of 5% rhodium on alumina and the reaction mixture was placed on the Parr hydrogenation apparatus maintained at 50 psi for 4 hrs. The reaction mixture was filtered through celite and the solids were washed with 100 ml of ethanol. The filtrated was concentrated in vacuo.

The crude product (176 mg) was chromatographed on 60 g of 230- 400 mesh silica gel. The column was packed and eluted with (90 0:9.1:0.9) chloroform/methanol/ammonia. An initial fraction of 150 ml was collected followed by 6 ml fractions. Based on their TLC homogeneity. fractions 160-290 were combined giving 117 mg of the title compound. NMR (CDCl₃, TMS): δ 3.6-3.4 (t), 3.35.2 9 (br), 2.85-2.2 (m). 2.2-0.75 (m) and 0.65 ppm (s).

EXAMPLE 10

N-[(3β,5α)-3-[3-(dimethylamino)propoxy]estran.17-yl]-1,3-diaminopropane

A 10 ml, 2-necked flask, equipped with a magnetic stirrer, was flame dried and then cooled in a nitrogen atmosphere. The flask was charged with 41 μl (0.5 mmol) of 1,3-diaminopropane dissolved in 1.5 ml of methanol. The pH of the solution was adjusted to 6.0 with glacial acetic acid. The solution was then treated with 35 ml of 3β-dimethyloaminoether-17-keto-steroid from Preparation 9 followed by 9 mg of sodium cyanoborohydride and the reaction mixture was refluxed for 5 hours. The reaction mixture was concentrated in vacuo.

The crude product (135 mg) was chromatographed on 8 g of 230-400 mesh silica gel. The column was packed and eluted with (85.7:-12.9:1.4) chloroform/methanol/ammonia. An initial fraction of 5 ml was collected, followed by 0.9 ml fractions. Based on their TLC homogeneity, fractions 35-54 were combined affording 14 mg of the title compound. NMR (CDCl₃, TMS): δ 3.6-3.45 (t, 2H), 3.3-3.1 (br, 1H), 2.8-2.65 (m), 2.6-2.25 (m), 2.4-2.3 (m), 2.2 (s), 2.10.8 (m) and 0.7 ppm (s, 3H). (PLA2)

FORMULAS

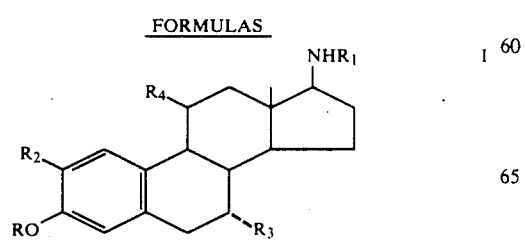

-continued
FORMULAS

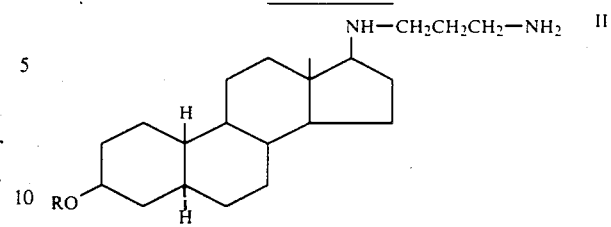 II

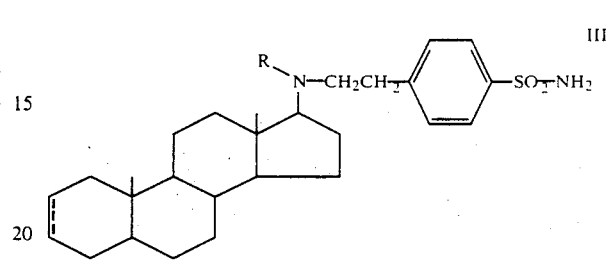 III

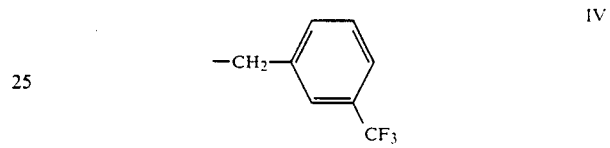 IV

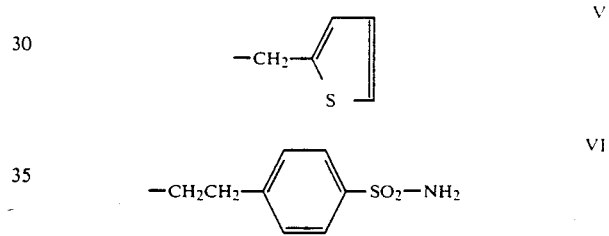 V

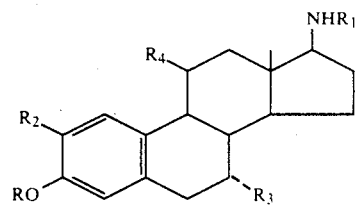 VI

We claim:
1. A compound of the formula

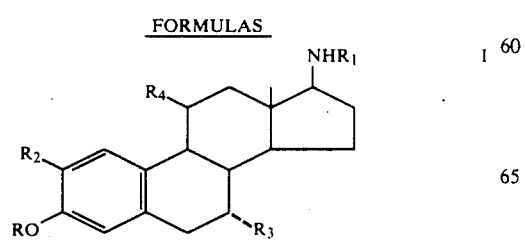 I wherein R is selected from the group consisting of
a. CH₂=CH—CH₂—,
b. HO—CH₂CH₂CH₂—, and
c. CH₃; and
wherein R₁ is selected from the group consisting of

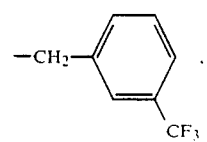 a.

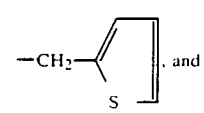, and b.

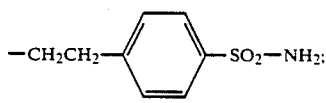

wherein $R_2$ and $R_3$ are methyl or hydrogen;

wherein $R_4$ is hydrogen or —OH;

and pharmacologically acceptable salts thereof.

2. A compound according to claim 1 selected from the group consisting of a. 3-methoxy-17β-[(2-thienylmethyl)-amino]-estra-1 3,5-(10)-triene, b. 3-Allyloxy-17β-[((3-trifluoromethyl)-phenylmethyl)amino-estra-1,3 5(10)-triene fumarate.

c. 3-(3-hydroxypropoxy) 17β-[((3-trifluoromethyl)-phenylmethyl) amino-estra-1,3,5(10)-triene fumarate, d. 3-Methoxy-7α-methyl-17β-[((3-trifluoromethyl)-phenylmethyl) amino-estra-1,3,5(10)-triene fumarate hydrate, e. 3-Methoxy-11β-hydroxy-17β[((3-trifluoromethyl)-phenylmethyl) amino-estra-1,3,5(10)-triene, and f. 2-methyl 3-methoxy-17β-[2-(4-amino-sulfonylphenyl)ethyl) amino]estra-1,3,5(10)-triene.

and pharmacologically acceptable salts thereof.

3. A compound of the formula

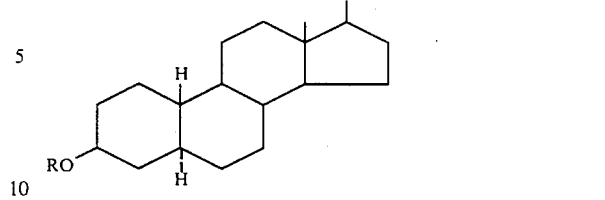

wherein R is a. $(CH_3)_2NCH_2CH_2CH_2$—, or b. $NH_2CH_2CH_2CH_2$—;

and pharmacologically acceptable salts thereof.

4. A compound according to claim 3 selected from a. N-[(3β,5α)-3-(3-aminopropoxy)-estran-17-yl]-1,3-propanediamine, and b. N-[(3β,5α)-3-[(dimethylamino) propoxy]estran-17-yl]-1,3-diaminopropane, and pharmacologically acceptable salts thereof.

5. A compound of the formula

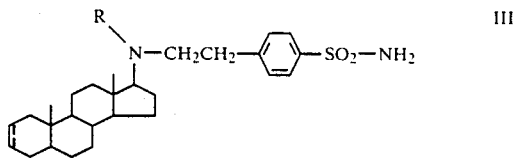

wherein the dashed line indicates that the 2-3 bond is saturated or unsaturated and, wherein R is hydrogen or methyl.

6. A compound according to claim 5 selected from a. N-methyl-17β-[2-(4-aminosulfonylphenyl)-ethyl)amino]-5α-androstane, and b. 17β-[2-(4-aminosulfonylphenyl)ethyl)-amino]-5α-androst-2-ene, and pharmacologically acceptable salts thereof.

* * * * *